US012607625B2

(12) United States Patent
Li et al.

(10) Patent No.: US 12,607,625 B2
(45) Date of Patent: Apr. 21, 2026

(54) METHOD FOR ELIMINATING INTERFERENCE OF THEOPHYLLINE IN IMMUNOASSAY AND IMMUNOASSAY KIT

(71) Applicant: SHENZHEN MINDRAY BIO-MEDICAL ELECTRONICS CO., LTD, Shenzhen (CN)

(72) Inventors: Ke Li, Shenzhen (CN); Chengxiong Zhan, Shenzhen (CN); Yuping Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 988 days.

(21) Appl. No.: 17/311,280

(22) PCT Filed: Dec. 6, 2018

(86) PCT No.: PCT/CN2018/119617
§ 371 (c)(1),
(2) Date: Jun. 4, 2021

(87) PCT Pub. No.: WO2020/113529
PCT Pub. Date: Jun. 11, 2020

(65) Prior Publication Data
US 2022/0018831 A1     Jan. 20, 2022

(51) Int. Cl.
*G01N 33/53*     (2006.01)
(52) U.S. Cl.
CPC ................................. *G01N 33/5306* (2013.01)
(58) Field of Classification Search
CPC ......... G01N 33/5306; G01N 33/54387; G01N 33/57484
USPC ....................................................... 436/501
See application file for complete search history.

(56) References Cited

U.S. PATENT DOCUMENTS 5,952,185 A     9/1999  Huber et al.

FOREIGN PATENT DOCUMENTS

| | | |
|---|---|---|
| CN | 102253215 A | 11/2011 |
| CN | 102892896 A | 1/2013 |
| CN | 104374905 A | 2/2015 |
| CN | 109100520 A | 12/2018 |
| JP | H04256854 A | 9/1992 |
| WO | WO 9532428 A1 | 11/1995 |

OTHER PUBLICATIONS

Tate et al., Interferences in Immunoassay, Clin Biochem Rev vol. 25 May 2004. (Year: 2004).*
Nordlund et al., Characteristics and clinical validity of two immunoassays for ProGRP, Tumor Biol., (2012), 33:1105-1113. (Year: 2012).*

* cited by examiner

*Primary Examiner* — Gregory S Emch
*Assistant Examiner* — Omar Ramadan
(74) *Attorney, Agent, or Firm* — Syncoda LLC; Feng Ma

(57)     ABSTRACT

The disclosure relates to a method for eliminating interference of theophylline in immunoassay and an immunodetection kit. The method for eliminating interference of theophylline in immunoassay includes: performing an immunoassay in the presence of a theophylline interference-resistant agent, the theophylline interference-resistant agent having a final concentration of 0.1 mg/mL-100 mg/mL, and being selected as at least one component from a group consisting of free 6-mercaptopurine, 6-thioguanine, 8-azguanine, hypoxanthine, adenine, purine, 2,6,8-trioxypurine, adenine nucleotide, and adenosine. The method and the kit can effectively reduce interference of theophylline on immunoassay results.

21 Claims, No Drawings

METHOD FOR ELIMINATING INTERFERENCE OF THEOPHYLLINE IN IMMUNOASSAY AND IMMUNOASSAY KIT

CROSS-REFERENCE TO RELATED APPLICATIONS

This application is a U.S. national phase entry of International Application No. PCT/CN2018/119617, filed Dec. 6, 2018, the content of which is incorporated herein by reference.

TECHNICAL FIELD

The disclosure relates to the field of immunoassay, in particular to a detection method for eliminating the influence of theophylline drugs in immunoassay for patients taking theophylline drugs.

BACKGROUND

Theophyllines, a class of anti-asthmatic drugs, have a direct relaxant effect on airway smooth muscles. Theophylline drugs are suitable for the treatment of asthma (such as bronchial asthma), chronic bronchitis, asthmatoid bronchitis, emphysema, chronic obstructive pneumonia and other diseases. They relax airways of the lungs and increase airflow, thereby alleviating the symptoms of wheezing. Theophyllines can also be used to treat wheezing in heart failure.

Within a certain time period after taking theophylline drugs, a certain amount of the drugs will remain in the patient's blood. In clinical immunoassay, if a certain concentration of a drug or its metabolites is present in blood of a subject, the accuracy of immunoassay results will be affected, and clinical judgment will thus be affected.

Therefore, there is a need for a method capable of eliminating interference of theophylline drugs in immunoassay for a subject.

SUMMARY

To this end, the disclosure provides a theophylline interference-resistant method in immunoassay and a theophylline interference-resistant immunoassay kit.

According to a first aspect of the disclosure, a method for eliminating theophylline interference in immunoassay of a sample includes: performing an immunoassay reaction in the presence of a theophylline interference-resistant agent, wherein the theophylline interference-resistant agent has a final concentration of 0.1 mg/mL to 100 mg/mL, and consists of at least one component selected from the group consisting of 6-mercaptopurine, 6-thioguanine, 8-azaguanine, hypoxanthine, adenine, purine, 2,6,8-trioxypurine, adenine nucleotide and adenosine.

According to a further embodiment, the final concentration of the theophylline interference-resistant agent is in a range of 5 mg/mL to 80 mg/mL, preferably 20 mg/mL to 80 mg/mL, and more preferably 50 mg/mL to 80 mg/mL.

According to a still further embodiment, the theophylline interference-resistant agent in the disclosure may comprise at least one component selected from the group consisting of 6-mercaptopurine, adenine, 2,6,8-trioxypurine and adenosine.

The method of the disclosure may be used in various immunoassays, especially in a chemiluminescence immunoassay, an electrochemiluminescence immunoassay or an enzyme-linked immunosorbent assay.

Specifically, the method of the disclosure relates to an immunoassay for a tumor marker, and more specifically to a solid-phase immunoassay.

According to one embodiment, in the disclosure, the theophylline interference-resistant agent may be added into the immunoassay reaction in the form of a separate reagent. For example, the theophylline interference-resistant agent is added to a sample to be tested in the form of a sample pre-processing solution before adding immunoassay reagents.

According to another embodiment, the theophylline interference-resistant agent of the disclosure is added into the immunoassay reaction in combination with one or more reagents. In the method of the disclosure, the one or more reagents include, but are not limited to: a substrate, a labeling substance, a solid phase coated with an immunoassay reactant, a sample processing solution, a buffer, an ionic strength adjuster, a surfactant, a preservative, a cleaning agent, etc.

According to a specific embodiment, the theophylline interference-resistant agent of the disclosure may be added before adding the substrate, preferably before adding the solid phase coated with the immunoassay reactant or before adding the labeling substance, and more preferably may be added during a sample pre-processing step.

In the method of the disclosure, the sample is a blood sample, and more specifically a serum sample or a plasma sample.

In a second aspect of the disclosure, an immunoassay kit is provided, wherein the immunoassay kit comprises a theophylline interference-resistant agent, and said theophylline interference-resistant agent has a final concentration of 0.1 mg/mL to 100 mg/mL, and the theophylline interference-resistant agent comprises at least one selected component from the group consisting of 6-mercaptopurine, 6-thioguanine, 8-azaguanine, hypoxanthine, adenine, purine, 2,6, 8-trioxypurine, adenine nucleotide and adenosine.

According to one embodiment, the immunoassay kit comprises a theophylline interference-resistant agent at a final concentration of 5 mg/mL to 80 mg/mL, preferably 20 mg/mL to 80 mg/mL, and more preferably 50 mg/mL to 80 mg/mL.

According to a further embodiment, the theophylline interference-resistant agent in the kit of the disclosure is at least one component selected from the group consisting of 6-mercaptopurine, adenine, 2,6,8-trioxypurine and adenosine.

The immunoassay kit of the disclosure may be any kit for an immunoassay, especially a chemiluminescence immunoassay kit, an electrochemiluminescence immunoassay kit or an enzyme-linked immunosorbent assay kit.

According to a specific embodiment, the immunoassay kit of the disclosure is an immunoassay kit for a tumor marker.

In the immunoassay kit of the disclosure, the theophylline interference-resistant agent may be provided in the kit in combination with one or more reagents in the kit, or in the form of a separate reagent.

The immunoassay kit of the disclosure further includes other necessary reagents for immunoassay. According to the needs of detection object and detection method, the immunoassay kit of the disclosure correspondingly comprises different reagents. The specific reagents contained in different immunoassay kits are well known to a person skilled in the art.

For example, generally, a common enzyme-linked immunosorbent assay kit or chemiluminescence immunoassay kit may further comprise a substrate, a labeling substance, and an immunoassay reactant, especially an immunoassay reactant coated onto a solid phase (such as antigen, antibody, streptavidin, etc.). The solid phase may be a magnetic bead, a plastic bead, or an ELISA (enzyme-linked immunosorbent assay) plate or strip.

According to different needs, the kit may further comprise a sample processing solution, a buffer, an ionic strength adjuster, a surfactant and/or a preservative, etc., but is not limited thereto.

The immunoassay kit of the disclosure is used for the detection of a blood sample. The blood sample may be a serum sample or a plasma sample.

In another aspect of the disclosure, an immunoassay method for eliminating theophylline interference is further provided. The immunoassay method has the features defined above and/or comprises the steps defined above.

In yet another aspect of the disclosure, provided is the use of a theophylline interference-resistant agent in eliminating theophylline interference in immunoassay of a blood sample, wherein the theophylline interference-resistant agent is at least one selected from the group consisting of 6-mercaptopurine, 6-thioguanine, 8-azaguanine, hypoxanthine, adenine, purine, 2,6,8-trioxypurine, adenine nucleotide and adenosine.

The methods and kits of the disclosure can significantly reduce or even eliminate interference caused by theophylline or metabolites thereof in immunoassay for subjects undergoing treatment with theophylline, so as to obtain more accurate immunoassay results free from theophylline interference, and provide reliable judgment basis for clinical diagnosis and treatment. The methods of the disclosure are simple and do not interfere with the immunoassay itself.

DESCRIPTION OF THE PREFERRED EMBODIMENTS

The technical solutions of embodiments of the disclosure will be described below clearly and completely in combination with specific embodiments and examples of the disclosure. Obviously, the embodiments described are merely some embodiments of the disclosure, not all embodiments of the disclosure. Based on the embodiments in the disclosure, all the other embodiments obtained by those of ordinary skill in the art without any creative efforts shall fall within the protection scope of the disclosure.

Throughout the specification, all terms used herein are intended to have their ordinary meaning in the art unless otherwise provided. Therefore, unless otherwise defined, all the technical and scientific terms used herein have the same meaning as commonly understood by those of skill in the art to which the disclosure belongs. In the event of a conflict, this specification takes precedence.

In this application, the terms "comprise", "include" or any other variation thereof are intended to cover non-exclusive inclusion, so that a method or product comprising a series of elements comprises not only explicitly recorded elements, but also other elements not explicitly listed, or elements inherent in implementing the method or product.

Unless otherwise specified, the singular forms "a/an" and "the/said" as used herein include the plural forms of the noun referred to.

The term "Theophylline" used herein, unless otherwise specified, includes any kind of theophylline drugs and all medicinal forms thereof.

Theophylline, as xanthine alkaloid, is a kind of drugs for relaxing bronchial smooth muscles and can be used for treatment of respiratory diseases such as bronchial asthma, chronic bronchitis, emphysema, and chronic obstructive pulmonary disease.

It is known that there are more than 300 theophylline drugs and derivatives thereof. Theophylline drugs commonly used in clinical include aminophylline, dihydroxypropyl theophylline, choline theophyllinate, theophylline ethanolamine, and enprofyline, but are not limited thereto.

The disclosure aims to provide methods for eliminating theophylline interference in immunoassay for subjects undergoing or having recently undergone treatment with theophylline.

The term "theophylline interference-resistant" or "eliminating theophylline interference" as used herein refers to reducing or even eliminating interference caused by theophylline drugs or metabolites thereof in immunoassay.

The term "subject" as used herein may be refer to a subject in need of immunoassay, who is being administered with theophylline or has recently been administered with theophylline, for example, a subject who has been administered with theophylline within 1 week, or within 5 days, 3 days or 2 days.

The term "sample" as used herein refers to a blood sample collected from a subject and used for immunoassay. Specifically, the sample is a serum or plasma sample, especially a serum sample.

The term "immunoassay", as used herein, unless otherwise specified, refers to a method for measuring the content of substance to be tested in a sample with the substance to be tested as antigen or antibody by using the principle of immunology.

Immunoassay methods used in the disclosure refer to immunoassay methods based on the principle of immune reaction, including, but not limited to:

enzyme-linked immunosorbent assay, radioimmunoassay, fluorescence immunoassay, chemiluminescence immunoassay, electrochemiluminescence immunoassay and the like. The methods and kits of the disclosure are especially suitable for an enzyme-linked immunosorbent assay, a chemiluminescence immunoassay and an electrochemiluminescence immunoassay.

The labeling substance varies according to specific methods, and is not particularly limited in the disclosure. Examples of labeling substance include antibodies (or antigens) labeled with enzymes (such as alkaline phosphatase, horseradish peroxidase), antibodies (or antigens, or immunoassay analytes) labeled with luminescent compounds (such as acridinium ester, luminol, isoluminol, ruthenium terpyridine, etc.), but are not limited thereto.

The methods of the disclosure are more suitable for a solid-phase immunoassay. The solid phase used in the solid-phase immunoassay of the disclosure may be a magnetic bead, a plastic bead, an immune plate (or strip), etc., which is coated with an immunoassay reactant. The immunoassay reactant coated onto the solid phase varies according to different methods, and may include, for example, an antigen, an antibody, streptavidin and the like.

The immunoassay methods of the disclosure for reducing theophylline interference are especially suitable for the immunoassay for a tumor marker.

Tumor markers are substances that exist in cancer cells, or are produced by cancer cells, or are produced by the body in response to cancer cells, and can reflect the presence, absence, and development of tumors. Therefore, the detection of tumor markers in serum can be used for tumor diagnosis, disease course analysis, determination of treatment plans, monitoring of tumor recurrence or metastasis, etc. There are many known tumor markers, including carbohydrate antigens, embryonic antigens, cytokeratins, tumor-related enzymes, hormones and other proteins. Examples of common tumor markers include: alpha-fetoprotein (AFP), carcinoembryonic antigen (CEA), carbohydrate antigen 125 (CA125), carbohydrate antigen 153 (CA153), carbohydrate antigen 199 (CA199), carbohydrate antigen 724 (CA724), carbohydrate antigen 242 (CA242), carbohydrate antigen 50 (CA50), CYFRA21-1 (Cy211), neuron specific enolase (NSE), prostate specific antigen (PSA), human chorionic gonadotrophin (HCG), thyroglobulin (TG), ferritin (SF), $\beta$2-microglobulin ($\beta$2-MG), squamous cell antigen (SCC), etc., but are not limited thereto.

The inventors have found that many purine compounds and derivatives thereof may reduce or even eliminate interference caused by theophylline or metabolites thereof in immunoassay. The purine compounds and derivatives thereof that may be used for the disclosure include 6-mercaptopurine, 6-thioguanine, 8-azaguanine, hypoxanthine, adenine, purine, 2,6,8-trioxypurine, adenine nucleotide and adenosine, wherein, 6-mercaptopurine, adenine, 2,6,8-trioxypurine and adenosine are preferable and have better effects.

In the disclosure, the final concentration of the theophylline interference-resistant agent is in a range of 0.1 mg/mL to 100 mg/mL. Specifically, the final concentration of the theophylline interference-resistant agent may be, for example, 6 mg/mL, 8 mg/mL, 10 mg/mL, 15 mg/mL, 20 mg/mL, 30 mg/mL, 40 mg/mL, 50 mg/mL, 60 mg/mL, 70 mg/mL or 80 mg/mL.

In a preferred embodiment, the final concentration of the theophylline interference-resistant agent is in a range of 5 mg/mL to 80 mg/mL, preferably 20 mg/mL to 80 mg/mL, and more preferably 50 mg/mL to 80 mg/mL.

According to the disclosure, the theophylline interference-resistant agent may be provided in the immunoassay kit of the disclosure or added to the immunoassay reaction as a separate reagent, or it may also be provided in the immunoassay kit of the disclosure or added to the immunoassay reaction in combination with one or more other reagents. Therefore, the concentration of the theophylline interference-resistant agent of the disclosure before being added to the immunoassay reaction depends on the form the agent is provided. In order to make the context clear and consistent, the term "final concentration" as used herein refers to the concentration in the immunoassay reaction, especially the concentration of the theophylline interference-resistant agent in the final immunoassay reaction.

According to one embodiment of the disclosure, the theophylline interference-resistant agent is provided in the form of a separate agent. Specifically, the theophylline interference-resistant agent is dissolved in an appropriate solvent to prepare a solution. The theophylline interference-resistant agent in the form of a separate reagent, as a sample pre-processing agent, and other sample processing solutions may be added to a sample to be tested sequentially or simultaneously. The theophylline interference-resistant agent may also be added during the detection reaction. For example, the theophylline interference-resistant agent is added to the reaction system before adding substrate, especially before adding solid phase coated with immunoassay reagent, or the labeling substance.

According to another embodiment of the disclosure, the theophylline interference-resistant agent is added to the immunoassay reaction system in combination (such as mixed) with other immunoassay reagents. For example, the theophylline interference-resistant agent may be added to a label-containing reagent, a substrate-containing reagent, or a solid-phase reagent. In addition, the theophylline interference-resistant agent may also be added to an auxiliary reagent, such as other sample-processing agent, buffer, ionic strength adjuster, surfactant, preservative, or cleaning agent. In short, a person skilled in the art may add the theophylline interference-resistant agent to a reagent that is easy to operate and has no adverse effects according to specific needs, so that the theophylline interference-resistant agent can be added to the immunoassay reaction system at an appropriate time to ensure that theophylline or metabolites thereof would not interfere with any reaction during the immunoassay.

Further provided in the disclosure is an immunoassay kit comprising the theophylline interference-resistant agent of the disclosure, so as to conveniently implement the methods of the disclosure.

The theophylline interference-resistant agent comprised in the kit of the disclosure is as defined above.

Similarly, the kit of the disclosure may be a kit for any immunoassay for a subject in need thereof, and is not particularly limited. However, the kit of the disclosure is particularly an enzyme-linked immunosorbent assay kit, a chemiluminescence immunoassay kit or an electrochemiluminescence immunoassay kit.

More specifically, the immunoassay kit of the disclosure is a detection kit for a tumor marker, and more preferably a kit for a solid-phase immunoassay.

Similarly, in the immunoassay kit of the disclosure, the theophylline interference-resistant agent may be present in the form of a separate reagent, or in combination (such as mixed) with one or more other reagents required for the immunoassay reaction.

The following examples are used to further illustrate the effects of the disclosure.

Example 1

In Example 1, the theophylline interference-resistant capability of the above-mentioned theophylline interference-resistant agent is evaluated.

First, two groups of serum samples containing pro-gastrin-releasing peptide (ProGRP) respectively at a concentration of (40.00±10.00) μg/mL and (600.00±120.00) μg/mL, respectively were prepared, and two samples for each group were prepared; a certain volume of a high-concentration theophylline solution was added to one sample in each group (wherein theophylline was dissolved in absolute ethanol, and the added volume did not exceed $\frac{1}{20}$ of the total volume after the addition) to prepare interferent samples containing theophylline at a concentration of 50 μg/mL; an equal volume of absolute ethanol was added to the other sample (the added volume was the same with that in the aforementioned interferent-containing samples, i.e., not exceeding $\frac{1}{20}$ of the total volume after the addition) to prepare control samples without interferent.

Chemiluminescence immunoassay kits for pro-gastrin-releasing peptide were used to test the interferent samples and the control samples twice respectively. The mean value of the test results of the interferent was recorded as M, the mean value of the test results of the control samples was recorded as T, and the interference deviation B was calculated according to the following equation:

$$B(\%)=(M-T)/T\times100\%.$$

In Example 1, the pro-gastrin-releasing peptide assay kits used for detection are commercially available kits or the kits of the disclosure which are prepared from commercially available kits to which a theophylline interference-resistant agent is added. Specifically, each commercially available kit comprises the following components:

a magnetic particle reagent, which includes superparamagnetic particles coated with anti-ProGRP antibodies, and suspended in a Tris buffer;

a labeling reagent, which includes anti-ProGRP antibody-alkaline phosphatase labels, dissolved in IVIES buffer; and a chemiluminescent substrate: 3-(2-spiroadamantane)-4-methoxy-4-(3-phosphoryloxy)-phenyl-1,2-dioxetane, AMPPD.

A theophylline interference-resistant agent of the disclosure at a final concentration of 10 mg/mL was added to the labeling reagent to prepare an immunoassay kit of the disclosure, wherein the theophylline interference-resistant agent is respectively as follows: 6-mercaptopurine, 6-thioguanine, 8-azaguanine, hypoxanthine, adenine, purine ($C_5H_4N_4$), 2,6,8-trioxypurine, adenine nucleotide or adenosine (9-$\beta$-D-ribofuranosyladenine).

In the magnetic particle reagent and labeling reagent of the above-mentioned kit, the antibodies can be coated onto the magnetic particles using conventional antibody-coating method, and the antibodies can be labeled with alkaline phosphatase using conventional labeling technology.

Kits containing different theophylline interference-resistant agents were used to detect pro-gastrin-releasing peptide, and the detection steps were as follows:

Step 1: 20 μL of a sample, along with 50 μL of the magnetic particle reagent and 50 μL of the labeling reagent was added to a reaction tube, and incubated at 37° C. for 10 minutes. After reaction was completed, a sandwich complex was formed, and magnetic beads were absorbed under magnetic field to wash away unbound materials.

Step 2: The chemiluminescent substrate (AMPPD) was added to the reaction tube and incubated at 37° C. for 6 minutes. The chemiluminescent substrate reacted with the alkaline phosphatase on the sandwich complex bound to the magnetic particles to generate luminescence, and the number of photons generated was proportional to the concentration of the pro-gastrin-releasing peptide in the sample, and the luminescence reading was recorded. The amount of the pro-gastrin-releasing peptide in the sample was calculated from calibration curve.

The above-mentioned kits containing different theophylline interference-resistant agents and kits without any theophylline interference-resistant agent were used for detection, and the interference deviations B obtained are shown in the following table.

| Theophylline interference-resistant agent | Final concentration of theophylline interference-resistant agent | Interference deviation of low-concentration samples | Interference deviation of high-concentration samples |
|---|---|---|---|
| None | / | −34.92% | −39.45% |
| 6-Mercaptopurine | 10 mg/mL | −2.24% | −1.04% |
| 6-thioguanine | 10 mg/mL | −5.63% | −3.66% |
| 8-Azaguanine | 10 mg/mL | −8.22% | −5.27% |
| Hypoxanthine | 10 mg/mL | −9.36% | −7.05% |
| Adenine | 10 mg/mL | 2.16% | −3.52% |
| Purine ($C_5H_4N_4$) | 10 mg/mL | −5.95% | −3.77% |

-continued

| Theophylline interference-resistant agent | Final concentration of theophylline interference-resistant agent | Interference deviation of low-concentration samples | Interference deviation of high-concentration samples |
|---|---|---|---|
| 2,6,8-Trioxypurine | 10 mg/mL | 3.52% | 2.18% |
| Adenine nucleotide | 10 mg/mL | 5.06% | 5.01% |
| Adenosine | 10 mg/mL | −0.17% | 1.16% |

From the results in the above table, it can be seen that when the concentration of the interferent theophylline in the sample reaches 50 μg/mL, the pro-gastrin-releasing peptide kit without the compounds listed in this method shows a larger interference deviation (−34.9% for the low-concentration samples, and −39.5% for the high-concentration samples), indicating that theophylline in the sample seriously interferes with the test results of the kit.

When the above-mentioned theophylline interference-resistant agent at a certain final concentration (10 mg/mL in this example) is added to one of the components of the kit, the interference deviation can be reduced to an acceptable range (within ±10%), effectively reducing interference of theophylline on the test results.

Example 2

In Example 2, the theophylline interference-resistant capability of the theophylline interference-resistant agent at different final concentrations is evaluated according to substantially the same method as that in Example 1.

In this example, purine at a final concentration of 1 μg/mL, 0.1 mg/mL, 1 mg/mL, 5 mg/mL, 10 mg/mL, 20 mg/mL, 50 mg/mL, 80 mg/mL and 100 mg/mL, was respectively added to the labeling reagent of the immunoassay kit for ProGRP, and then by using the same method as that in Example 1, serum samples containing pro-gastrin-releasing peptide (ProGRP) at a concentration of (40.00±10.00) pg/mL and (600.00±120.00) pg/mL, respectively, with 50 μg/mL of theophylline interferent or without any interferent were detected, and the interference deviations B were calculated. The results are shown in the following table.

| Final concentration of theophylline interference-resistant agent | Interference deviation of low-concentration samples | Interference deviation of high-concentration samples |
|---|---|---|
| 0 | −34.92% | −39.45% |
| 1 μg/mL | −28.11% | −38.29% |
| 0.1 mg/mL | −9.33% | −9.40% |
| 1 mg/mL | −8.06% | −8.23% |
| 5 mg/mL | −7.92% | −7.50% |
| 10 mg/mL | −5.95% | −3.77% |
| 20 mg/mL | −4.06% | −2.19% |
| 50 mg/mL | −2.00% | −1.68% |
| 80 mg/mL | −1.09% | −0.88% |
| 100 mg/mL | 1.58% | 3.14% |

It can be seen from the results in the above table that purine at different final concentrations can reduce or even eliminate interference caused by theophylline in immunoassay to varying degrees. With the successive increasing concentration of purine added to the pro-gastrin-releasing peptide kit, the interference deviation of the interferent samples containing theophylline at a concentration of 50 μg/mL successively decreases; when the concentration of purine added increases to a final concentration of about 0.1 mg/mL, the interference deviation can be reduced to an acceptable range (within ±10%), that is, interference of theophylline on the test results is significantly reduced. As the final concentration of purine further increases, the absolute deviation of theophylline interference-resistance further decreases. When the final concentration of purine reaches 20 mg/mL, the influence on the deviation of the detection results is relatively reduced as the concentration of purine increases.

The invention claimed is:

1. An immunoassay method, the method comprising:
providing a blood sample;
providing an immunoassay kit comprising a substrate, a labeling substance, and a solid phase coated with an immunoassay reactant;
performing an immunoassay of the blood sample using the immunoassay kit in the presence of a theophylline interference-resistant agent,
wherein the theophylline interference-resistant agent reduces interference caused by theophylline in the immunoassay;
wherein the theophylline interference-resistant agent is 6-mercaptopurine, 6-thioguanine, 8-azaguanine, hypoxanthine, purine, or adenosine;
wherein the theophylline interference-resistant agent has a final concentration of 10 mg/mL to 100-80 mg/mL; and
detecting the level of pro-gastrin-releasing peptide in the blood sample.

2. The immunoassay method of claim 1, wherein the final concentration of the theophylline interference-resistant agent is in a range of 20 mg/mL to 80 mg/mL.

3. The immunoassay method of claim 1, wherein the theophylline interference-resistant agent is 6-mercaptopurine, or adenosine.

4. The immunoassay method of claim 1, wherein the immunoassay kit further comprises one or more of a sample processing solution, a buffer, an ionic strength adjuster, a surfactant and a preservative.

5. A method for reducing interference of theophylline in an immunoassay for detecting pro-gastrin-releasing peptide of a sample, the method comprising:
performing an immunoassay reaction in the presence of a theophylline interference-resistant agent,
wherein the theophylline interference-resistant agent reduces interference caused by theophylline in the immunoassay;
wherein the theophylline interference-resistant agent has a final concentration of 0.1 mg/mL to 80 mg/mL, and
wherein the theophylline interference-resistant agent is 6-mercaptopurine, 6-thioguanine, 8-azaguanine, hypoxanthine, purine, or adenosine; and
detecting the level of pro-gastrin-releasing peptide in the blood sample.

6. The method of claim 5, wherein the final concentration of the theophylline interference-resistant agent is in a range of 5 mg/ml to 80 mg/mL.

7. The method of claim 5, wherein the theophylline interference-resistant agent is 6-mercaptopurine, or adenosine.

8. The method of claim 5, wherein the immunoassay is a solid-phase immunoassay.

9. The method of claim 5, wherein the theophylline interference-resistant agent is added into the immunoassay reaction in the form of a separate reagent, or the theophylline interference-resistant agent is added into the immunoassay reaction in combination with one or more reagents.

10. The method of claim 5, wherein the theophylline interference-resistant agent is added into the immunoassay reaction before adding a substrate.

11. The method of claim 5, wherein the theophylline interference-resistant agent is added during a sample pre-processing step.

12. The method of claim 5, wherein the theophylline interference-resistant agent is added into the immunoassay reaction before adding a solid phase coated with an immunoassay reactant or before adding a labeling substance.

13. The method of claim 5, wherein the sample is a blood sample or a serum sample or a plasma sample.

14. The method of claim 1, wherein the blood sample is from a subject undergoing treatment with theophylline.

15. The method of claim 5, wherein the blood sample is from a subject undergoing treatment with theophylline.

16. The method of claim 1, wherein the level of pro-gastrin-releasing peptide detected in the blood sample serves as a basis for clinical diagnosis and treatment.

17. The method of claim 1, wherein the reduction of theophylline interference in the immunoassay is confirmed by an interference deviation of ±10%.

18. The method of claim 17, wherein the interference deviation (B) is calculated according to the following equation: $B(\%)=(M-T)/T\times100\%$, wherein M is the mean value of the test results of theophylline and T is the mean value of the test results of the control samples.

19. The method of claim 5, wherein the level of pro-gastrin-releasing peptide detected in the blood sample serves as a basis for clinical diagnosis and treatment.

20. The method of claim 5, wherein the reduction of theophylline interference in the immunoassay is confirmed by an interference deviation of ±10%.

21. The method of claim 20, wherein the interference deviation (B) is calculated according to the following equation: $B(\%)=(M-T)/T\times100\%$, wherein M is the mean value of the test results of theophylline and T is the mean value of the test results of the control samples.

\* \* \* \* \*